United States Patent [19]
Muhlberg et al.

[11] Patent Number: 5,283,623
[45] Date of Patent: Feb. 1, 1994

[54] METHOD AND SYSTEM FOR THE DETECTION OF FAULTS IN A LENGTH OF TEXTILE

[75] Inventors: Karl-Heinz Muhlberg, Dornstetten; Friedrich Weber, Altensteig, both of Fed. Rep. of Germany

[73] Assignee: Memminger-IRO GmbH, Dornstetten, Fed. Rep. of Germany

[21] Appl. No.: 937,590

[22] Filed: Aug. 31, 1992

[30] Foreign Application Priority Data

Sep. 2, 1991 [DE] Fed. Rep. of Germany ....... 4129126

[51] Int. Cl.⁵ ...................... G01N 21/00; G01N 21/84
[52] U.S. Cl. ................................... 356/238; 356/430; 250/562; 250/572
[58] Field of Search ............... 356/238, 237, 429, 430, 356/431; 250/562, 563, 571, 572

[56] References Cited

U.S. PATENT DOCUMENTS

| | | | |
|---|---|---|---|
| 3,958,127 | 5/1976 | Faulhaber et al. | 250/572 |
| 4,075,498 | 2/1978 | Takasuda et al. | 356/238 |
| 4,110,048 | 8/1978 | Akutsu et al. | 356/431 |
| 4,748,334 | 5/1988 | Kobayashi et al. | |
| 4,952,062 | 8/1990 | Bean, III et al. | 356/430 |
| 5,006,722 | 4/1991 | Adelson | 356/430 |

FOREIGN PATENT DOCUMENTS

| | | |
|---|---|---|
| 1938677 | 7/1969 | Fed. Rep. of Germany . |
| 2644502 | 4/1977 | Fed. Rep. of Germany . |
| 3133428 | 6/1982 | Fed. Rep. of Germany . |
| 4001650 | 8/1990 | Fed. Rep. of Germany . |

*Primary Examiner*—Richard A. Rosenberger
*Assistant Examiner*—Hoa Q. Pham
*Attorney, Agent, or Firm*—Frishauf, Holtz, Goodman & Woodward

[57] ABSTRACT

In a method and system for the detection of faults in a length of textile fabric, the length of fabric is continuously scanned by an electro-optical sensor head. Light detectors located in a strip-form sensing zone of the sensor head are assembled in groups and emit group-specific fault signals. These fault signals are analyzed multi-dimensionally for the identification of spot faults and/or long faults, the criteria for analysis being the signal amplitude, the signal length, the recurrence of the signals and their periodic repeat at each revolution of the machine. Display, control counter devices and the like are energized as a function of the result of the analysis.

20 Claims, 9 Drawing Sheets

METHOD AND SYSTEM FOR THE DETECTION OF FAULTS IN A LENGTH OF TEXTILE

Reference to related publications: German Patents 1 938 677; 3 133 428; 3 536 991; 4 001 650; 2 644 502.

FIELD OF THE INVENTION

The invention relates to a method and system for the detection of faults in a length of textile fabric, especially in a knitted fabric of tubular form produced on a circular knitting or circular warp knitting machine.

BACKGROUND

It is known to electro-optically scan the length of fabric in at least one zone of strip form by sensing means, which for recording the state of the fabric emit electrical identifier sensing signals at a number of sensing points lying within the strip-form zone, which for the purpose of identifying faults are analyzed in such a way that distinction is made between different forms and/or sizes of different types of fault. Separate output signals are produced for types of fault detected in this way and for energizing display and/or control or switching devices. A relative movement of predetermined speed in a direction transverse to the strip-form zone is maintained between the length of fabric and the sensing means during scanning. Zones of the length of fabric to be scanned are preferably scanned a number of times.

In high-speed circular knitting machines for example there is a need for the tubular fabric being taken off continuously during operation to be monitored for the occurrence of faults. These faults may be "spot" faults, i.e. "holes" as caused for example by a thread break and running transversely to the lengthway direction of the tubular fabric, mainly over several wales of stitches. There can also be "long" faults, however, i.e. faults which extend longitudinally along the tubular fabric over several courses of stitches and typically occur as "runs". With spot faults occurring only spasmodically such as when knitting yarns of inferior quality, or with "long" faults of relatively short length, it is often not worthwhile stopping the machine. It is desirable, however, to record the number of these faults occurring for instance per unit time or in the fabric roll. However, if runs suddenly start to occur in the tubular fabric which extend over a considerable length, then this a sign of a needle breakage having occurred and that the machine needs to be stopped as quickly as possible.

A variety of textile monitoring devices with electro-optical sensing heads and associated analysis units are known for the continuous monitoring of a length of textile fabric, especially a tubular knitted fabric produced on a circular knitting or warp-knitting machine. These sensing heads operate with light sources and light detectors in the form of photocells, frequently arranged in rows and responding to the change in the reflectance status of the fabric occurring consequent upon a fabric fault and emitting corresponding signals. These signals are analysed by the various known methods according to a variety of criteria. When the result of the analysis exceeds a prescribed tolerance value the machine is switched off.

Many of the previously known sensing devices have the disadvantage that although they respond generally to spot faults and long faults, they are unable to undertake any reliable fault discrimination according to the type of fault involved. In order to prevent unnecessary interruptions in the knitting process, however, it is advisable to prescribe a permissible fault rate and only emit a stop signal to the machine on reaching this fault rate.

Greater importance is thereby attached to the detection of long faults in the form of runs, dropped stitches, pulled stitches, i.e. faults which cause a fault to be recorded repeatedly at every revolution of the machine. As already mentioned, long faults of considerable length are invariably due to a needle defect at the point of stitch formation, which it is essential to correct quickly to prevent faulty lengths of knitted fabric.

On the other hand, however, abortive stoppages for short-term fault phenomena in the knitted fabric (e.g. thick or thin places in the yarn, trash in cotton etc.) must be positively prevented, as they adversely affect the productivity of the knitting machine and largely represent an interference factor. Examples of such known devices and methods for monitoring a length of textile fabric with electro-optical sensing heads may be found in a number of publications:

From DE-OS 1 938 677 a run detector for circular knitting and warp-knitting machines is known which is arranged within the tubular knitted fabric and which has a light beam source together with at least one photodiode as the beam detector, which are arranged at uniform distance from the tubular fabric and of which the photodiode is located in relation to the beam source in such a way that it is incapable of detecting any direct illumination from the beam source. Suggested sources of illumination here are standard light sources or luminescence diodes operating in the infrared zone. Details of how the control circuit which analyses the signals emitted by the light detectors is designed are not disclosed.

In a method known from DE-PS 3 133 428 for detecting and analysing faults in textiles, especially in knitted fabrics, a number of emitter heads are used, in which the signal analysis circuit comprises a microcomputer. A textile fabric monitoring device similarly operating with a microprocessor in accordance with DE-PS 3 536 991 permits automatic adjustment of its sensitivity to the level of reflectance of the length of textile to be monitored, in order thereby to improve the confidence level of the fault record. A number of infrared light diodes arranged in a row are used as pulsed light emitters.

In a method known from DE-OS 4 001 650 for monitoring faults in a length of textile fabric, especially on circular knitting machines for detecting runs, bars, needle stripes and holes, precautionary measures are provided so that regardless of the speed of the machine, the fault monitoring device is calibrated automatically and the machine switch-off is actuated only in the case of a fault being detected repeatedly at the same point. The number of repeated occurrences of a fault needed for switch-off can be adjusted as required. However, to prevent unnecessary stoppages only faults of the nature of a run are intentionally considered. The electro-optical sensor comprises infrared diodes and phototransistors arranged alternately in a row.

Finally a device is known from DE-OS 2 644 502 for detecting holes in a piece or length of fabric.

This system is intended to discriminate between holes extending transversely to the direction of travel of the fabric, i.e. holes of the nature of a run and relatively small holes. For this purpose electro-optical sensing means are used which incorporate a slot arranged transversely to the direction of travel of the fabric and on which a number of photocells are arranged, the output signals of which are compared with each other. An analysis circuit compares the output signal of each photocell with the mean of the output signals of the remaining photocells and identifies on a symmetrical or an asymmetrical signal distribution the presence of a spot fault or long fault. The identification of long faults (runs) and their differentiation from holes is not possible by this means with a sufficient confidence level, because it is assumed that the long faults run exactly parallel to the photocells arranged in a perpendicular row. Such a requirement is practically impossible to satisfy on a circular knitting machine, however, because the tubular fabric with its initial cylindrical shape must of course be laid flat for takeup on the fabric roll. If a run lying only slightly obliquely to the row of photocells passes, then consecutive staggered individual signals are produced in the latter, the result of which is that the run is erroneously interpreted as holes occurring in quick succession.

THE INVENTION

It is an object to detect faults with a greater confidence level in the distinction between spot faults and long faults, especially in the tubular fabric produced by a circular knitting machine, whilst simultaneously substantially eliminating abortive stoppages.

Briefly, the identifier sensing signals for the individual sensing points are respectively collected in group form into at least two fault signals, which are processed and analyzed separately, so that in this analysis the amplitude value, the signal term, i.e. its time duration, and the individual or collective occurrence of fault signals of the individual groups are measured or established, and that from this an analysis is undertaken in such a way that
a) the fault is identified as a spot fault if in at least one fault signal with its amplitude value deviating from a prescribed first amplitude threshold value, its signal duration or term exceeds a prescribed first time threshold value and at least one predetermined longer term, without several fault signals occurring together within a measuring period;
b) the fault is identified as a long fault if in at least two fault signals with their amplitude values deviating from a prescribed second amplitude threshold value the signal duration or term exceeds a prescribed second time threshold value by at least one predetermined shorter term and at least two fault signals occur together within one measuring period; and otherwise
c) no fault is identified.

This method performs a discriminating multi-dimensional analysis of the fault signals in accordance with various criteria which together ensure that a correct distinction is made between spot fault or "hole" and long fault or "run".

The first and second amplitude threshold values may be equal or of different levels. As the two types of fault are analysed separately it is as a general rule advisable with long faults to operate at a higher sensitivity threshold than with spot faults, and therefore without having to expect abortive stoppages from this cause. Experience shows in fact that spot faults (holes) produce a higher fault signal amplitude, which permits the means to be found for identifying these faults with a lower sensitivity threshold.

By adopting at least two different sensitivity thresholds it is also possible to distinguish marginal faults which are due to irregularities in the knitted fabric.

Analysis of the signal term of the fault signals obtained in the evaluation is based on the knowledge that spot faults (holes) as a general rule extend over a number of wales, i.e. they are "wider" than runs. Runs on the other hand are usually restricted to one wale.

By the adoption of suitable amplitude threshold values and time threshold values for the signal term, minor irregularities and electrical interference signals are eliminated in fault detection.

As the individual or collective occurrence of fault signals within a prescribed measuring period (logic window) is determined, any time shift of the sensing signals emanating from the individual sensing means collected into groups, due for example to an oblique alignment of a run in relation to the strip-form sensing zone, does not result in an erroneous interpretation of "several consecutive holes" instead of "long fault". In a practical embodiment of this evaluation stage the fault signals can each be held individually in an interim memory at least over a predetermined period of time and only then investigated for repeated occurrence.

In association with the above-mentioned criteria there is finally the establishment of whether the AND-requirement or the OR-requirement is satisfied in the occurrence of the fault signals for the positive identification of the type of fault involved. In principle a fault signal only results in machine stoppage if the type of fault after analysis satisfies the criteria appropriate to the respective type of fault.

The sensing signals produced by the electro-optical sensing means can be utilised not only for identifying faults but also for monitoring the optical sensing conditions of the fabric. For instance it is possible for a weighted cumulative signal to be produced from these sensing signals in order to calibrate automatically the electro-optical sensing means to constant prescribed optical sensing conditions as a function of this cumulative signal. This calibration is accomplished preferably by a pulse-form control of the current emitted by the light sources, in such a way that the light detectors (photo-transistors) operate constantly within their optimum operational range.

This weighted cumulative signal can be further monitored for whether it lies within prescribed tolerances, and if one of these tolerances is exceeded a control signal is emitted. In this way it may be detected whether defects are present in the area of the sensing means, e.g. a sensor head, for example lamp failure, fitting fault, strong extraneous light, control failure etc.

DRAWINGS

In the drawing a fault monitoring device operating by the method in accordance with the invention for the tubular fabric produced by a circular knitting machine is shown as an embodiment example. The following are represented in diagram form.

DETAILED DESCRIPTION

Figure 1:
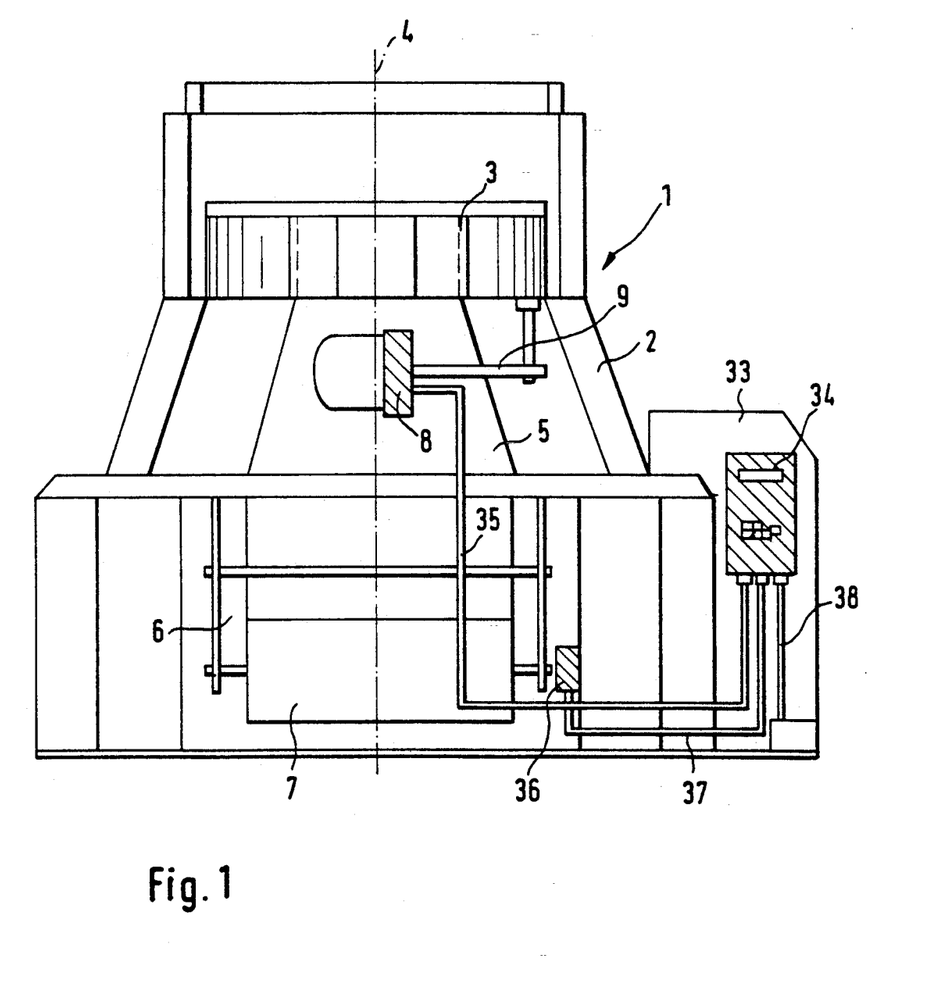
FIG. 1 a circular knitting machine with a fault monitoring device fitted, in basic diagram form and in side elevation, FIG. 2 the electro-optical sensing head of the fault monitoring device in accordance with FIG. 1, in axial section in side elevation, FIG. 3 a block circuit diagram of the electrical circuit of the sensing head in accordance with FIG. 2, FIG. 4 a block circuit diagram of the electronic signal analysis circuit of the fault monitoring device in accordance with FIG. 1, FIG. 5 the front panel on the operating side of the control unit of the fault monitoring device in accordance with FIG. 1, in diagram form and in plan view and on a different scale, and FIGS. 6 to 9 the flow diagram of the order of events of a programme on the microcomputer of the signal analysis circuit of the fault monitoring device in accordance with FIG. 4.

The circular knitting machine 1 represented in diagram form in FIG. 1 has a machine frame 2 in which a needle cylinder indicated at 3 is rotatably mounted on a vertical axis 4. The multi-feed circular knitting machine produces a tubular fabric 5 revolving around the vertical axis 4, which is drawn off by the conventional positive cloth take-up device 6 and continuously rolled up lying flat into a roll of fabric 7.

The revolving knitted or warp-knitted tubular fabric 5 is continuously monitored for faults by an electro-optical sensor head 8 located in a stationary position underneath the needle cylinder 3. The sensor head 8 can be located inside or outside the tubular fabric 5 according to the type of machine. In the embodiment example shown scanning of the tubular fabric 5 takes place from the outside inwards; the sensor head 5 is therefore fitted by a bracket 9 to the machine frame 2 in such a way that it is able to move somewhat in cushioned fashion in relation to the knitted structure of the tubular fabric 5.

Figure 2:
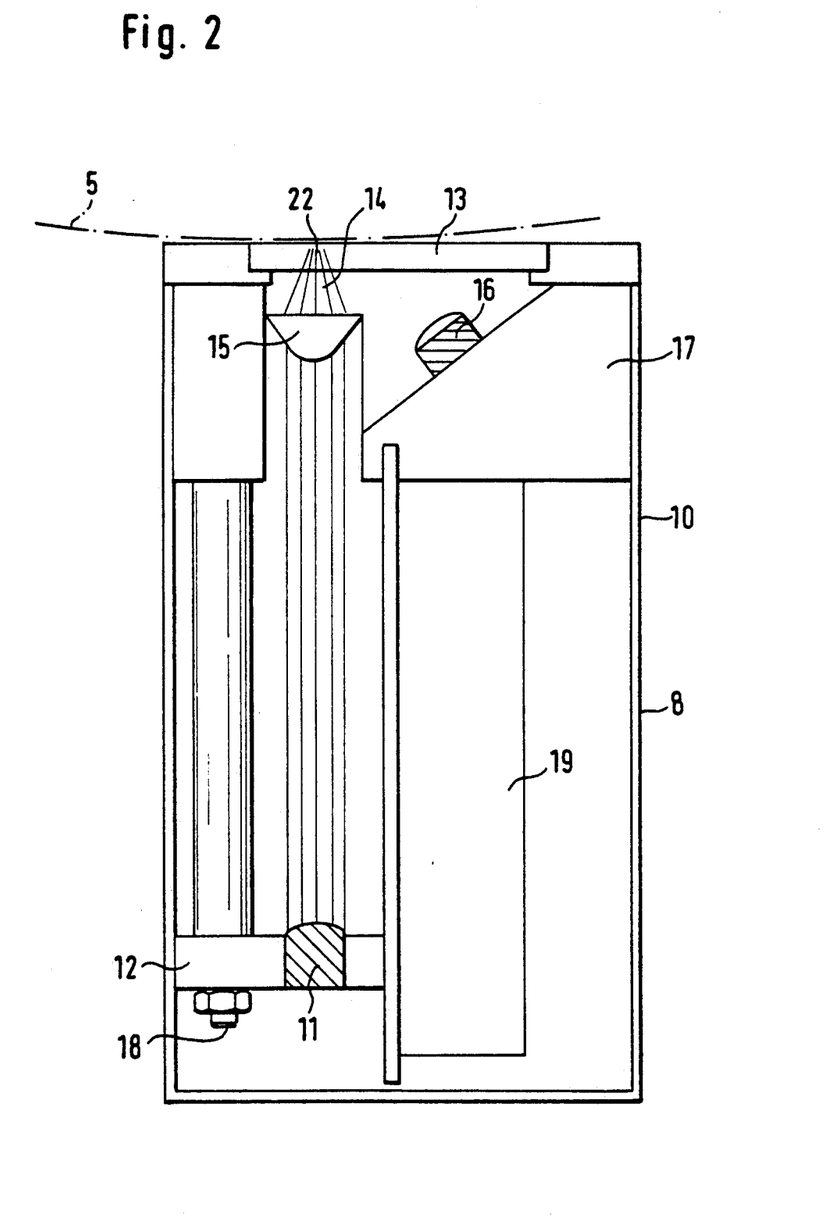

As represented in diagram form in FIG. 2, the sensor head 8 has a housing 10 approximately of box form in which a number (in the present case six) light sources 11 are arranged in a row extending perpendicularly to the plane of the paper on an associated bracket 12. The light emitted from the light sources 11 and focussed in each case by a condenser lens 15 passes through a transparent disc 13, laterally shielded in strip form, and forming the face of the housing 10, onto the knitted structure of the length of fabric indicated at 5. The light reflected by the latter passes through the transparent disc 13 and a lens similar to lens 15 in the housing 10 also exposed to the light sources 11 to (in the present case six) light detectors 16, which are in the form of phototransistors and are arranged in a row corresponding to the row of light sources 11 and mounted on a bracket 17, which is held stationary by bolts 18 in the housing 10. The housing 10 of the sensor head 8 also contains electronic modules for the processing of the sensing signals emitted by the light detectors 16 and for the automatic brightness regulation of the light sources 11. The associated circuit board is indicated by 19. Its circuit design is explained in the following in association with FIG. 3.

The focussed light emitted by the individual light emitters 11 is reflected by the textile surface of the length of fabric 5 being scanned and passes to the light detectors 16, which via output lines 20 supply to a signal processing circuit 21 electrical sensing signals which characterise the status of the reflecting textile fabric at the respective sensing points. These sensing points lie within a zone of strip form defined by the row arrangement of the light sources 11 and the light detectors 16, which is indicated at 22 in FIG. 2 and which extends transversely to the direction of rotation of the tubular fabric 5. This zone of strip form is therefore aligned approximately parallel to the vertical axis 4 in FIG. 1.

In this each of the light detectors 16 lying in a row forms a discrete sensing point.

In the signal processing circuit 21 the signal outputs of the (in this case six) light detectors 16 arranged in a row are assembled into two groups each of three signal outputs. This grouping is performed for example in such a way that the three adjacent light detectors situated in the top row are allocated to one group I and the three light detectors in the bottom row are allocated to a second group II. In principle it also conceivable, however, to make the group allocation differently, for example in such a way that the light detectors 16 are allocated alternately to group I and group II, whereby progressive sensing of the length of fabric 5 passing by the sensor head may be achieved.

The number of groups into which the light sources 11 and the light detectors 16 are assembled is not restricted to two groups; a larger number may also be adopted depending on the respective sensing circumstances and the conditions of use of the sensor head 8.

The collection of the signal outputs of the light detectors 16 contained in a group takes place in the signal processing circuit 21 in such a way that whenever one of the light detectors 16 in one of the groups, i.e. in the present case in group I or group II responds and emits a sensing signal, a fault signal is emitted to a first signal line 23 allocated to group I or to a second signal line 24 allocated to group II.

In order to ensure precise scanning of the length of textile fabric 5 and to prevent abortive machine stoppages due to sensing errors, the optical sensing conditions in the scanning zone must be kept as constant as possible. The textile surface in the scanning zone of the light sources 11 is therefore illuminated at a defined brightness. In order to compensate changes in environmental conditions (room illumination, shadows etc.) an automatic brightness regulation is provided which is incorporated in the sensor head 8.

Figure 3:
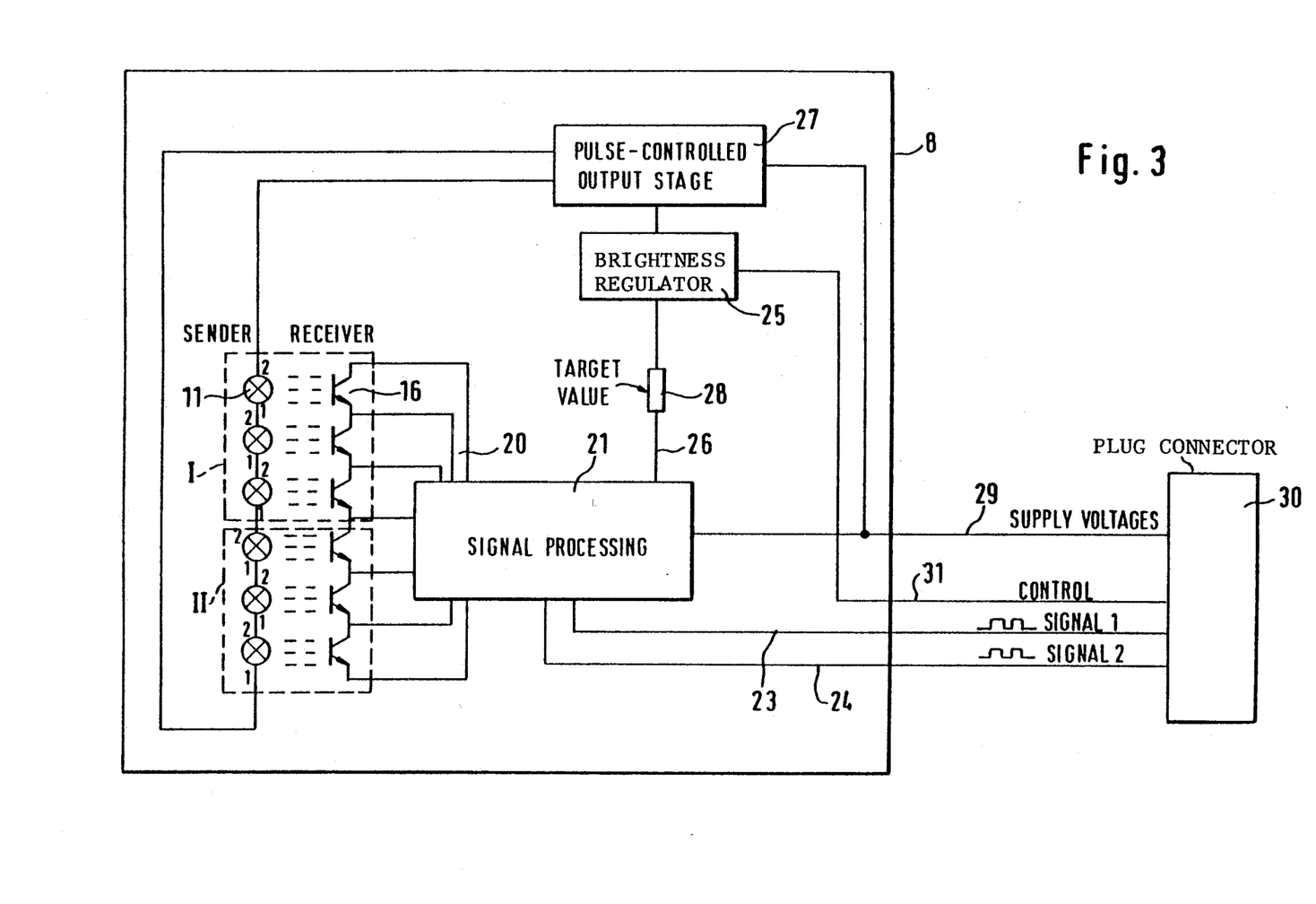

As may be seen from FIG. 3, the sensor head 8 contains a brightness regulator 25 to which a weighted cumulative signal derived from the output signal of the light detectors 16 is passed at 26 by the signal processing circuit 21 and which by a pulse-controlled output stage 27 adjusts to a prescribed target value the emitted current of the light sources 11 connected in electrical series, in such a way that the light detectors 16 (phototransistors) constantly operate in their optimum operational range. This range is determined by the target value prescribed, which can be set by means of a target value generator indicated at 28 and which normally remains unchanged. Regulation of the brightness of the light sources 11 is performed in known manner by a pulse width control in the output stage 27 of the pulse-form control current of the light sources 11, the frequency of which is about 20 to 30 kHz.

The power supply of the signal processing circuit 21 and of the light sources 11 or the pulse-controlled output stage 27 is via a power supply line 29, which together with the two signal lines 23, 24 is taken to a plug connector 30.

The plug connector 30 also accepts a further control line 31 from the brightness regulator 25, via which the control current supplied by the brightness regulator 25 of the pulse-controlled output stage 27 is monitored. When this control current exceeds or falls below prescribed limits, this is an indication that faults are present in the actual sensor head 8 such as lamp failure, fitting fault, strong extraneous light, control failure etc., which require immediate attention. These faults present in the sensor head 8 are thus similarly identified via the weighted cumulative signal produced in the signal processing circuit 21 from the output signals of the light detectors 16, which the signal processing circuit 21 supplies to their brightness regulators 25.

The circular knitting machine 1 in the manner shown in FIG. 1 has a control device 34 fitted for instance to the drive case 33 which contains the signal analysis circuit for the sensor head 8 and which is connected to the latter via a group of lines 35 containing lines 23, 24, 29, 31 (FIG. 3) and to which also is connected on the input side a pulse generator 36 fitted to the machine frame 2, which supplies the control device 34 with machine timing pulses via a line 37. Finally the mains supply line of the control device 34 is indicated by 38. The pulses from generator 36 determine the time windows, or terms, and relate lengths of possible faults to time, and movement of the fabric.

The control device 34 incorporates the analysis circuit for the fault signals which are supplied by the sensor head 8, and which will be explained in further detail with the aid of FIG. 4. It is also equipped with the elements necessary for operating the entire fault monitoring device. These include, as may be seen from the representation of the front panel 40 of the control device 34 in FIG. 5, a visual display field 41 for the current operational data and the menu control with corresponding entry keypad 42. A V24 interface 43 acts as a link with an external data recording device and/or a master computer system, as indicated at 44 in FIG. 4. By this means it is also possible to transfer the fault parameters The visual display field 41 is as a rule in the form of a two-column display on which the respective fault reports and any operational status of interest can be made clearly visible. Other forms of this display field are also conceivable of course. The purpose of the keyboard of the entry keypad 42 is to enter or interrogate specific values necessary for the general operational procedure.

Figure 5:
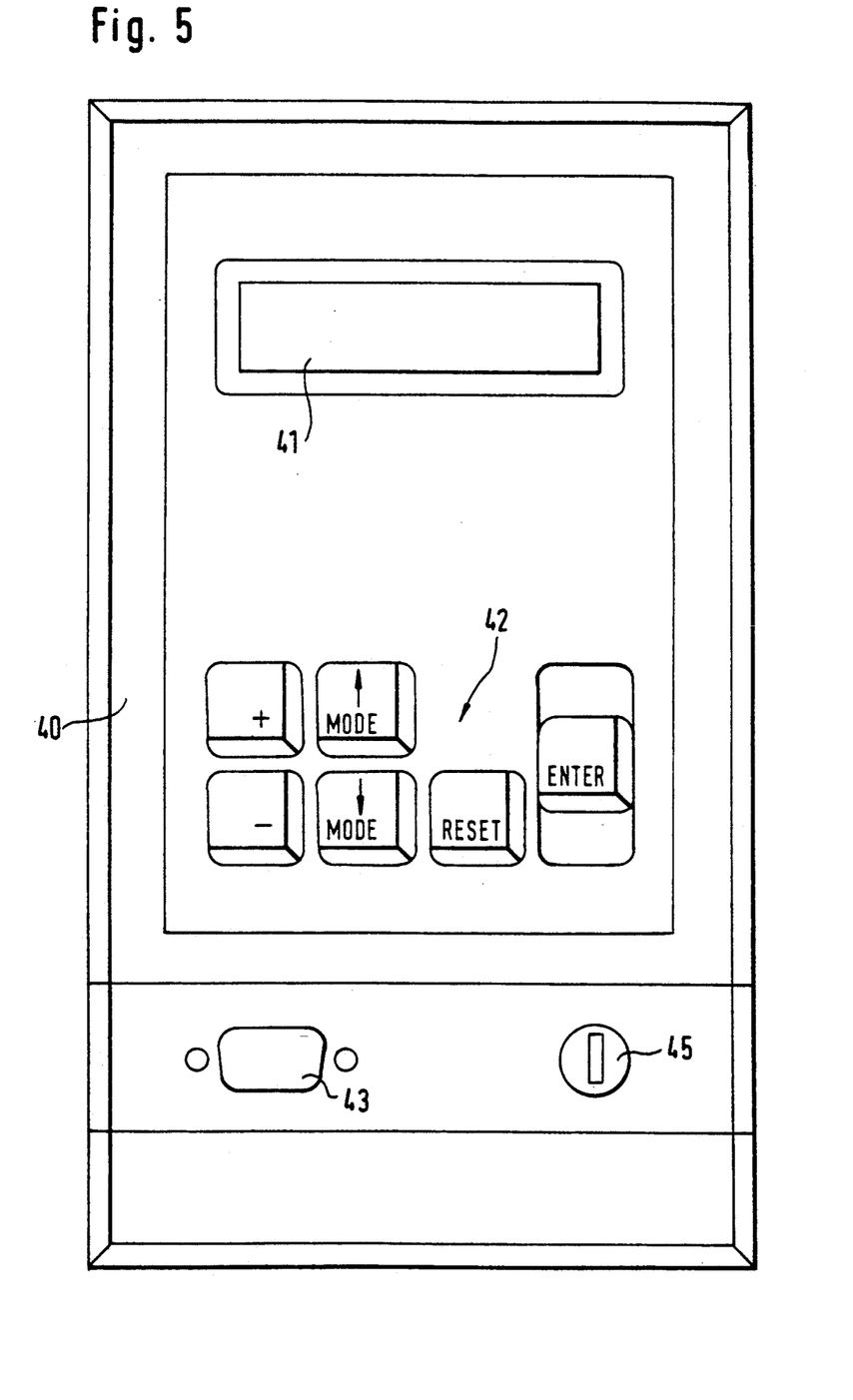

Finally the purpose of a key switch 45 provided in the lower part of the front panel is to prevent unauthorised access to the keyboard of the entry keypad 42.

Figure 4:
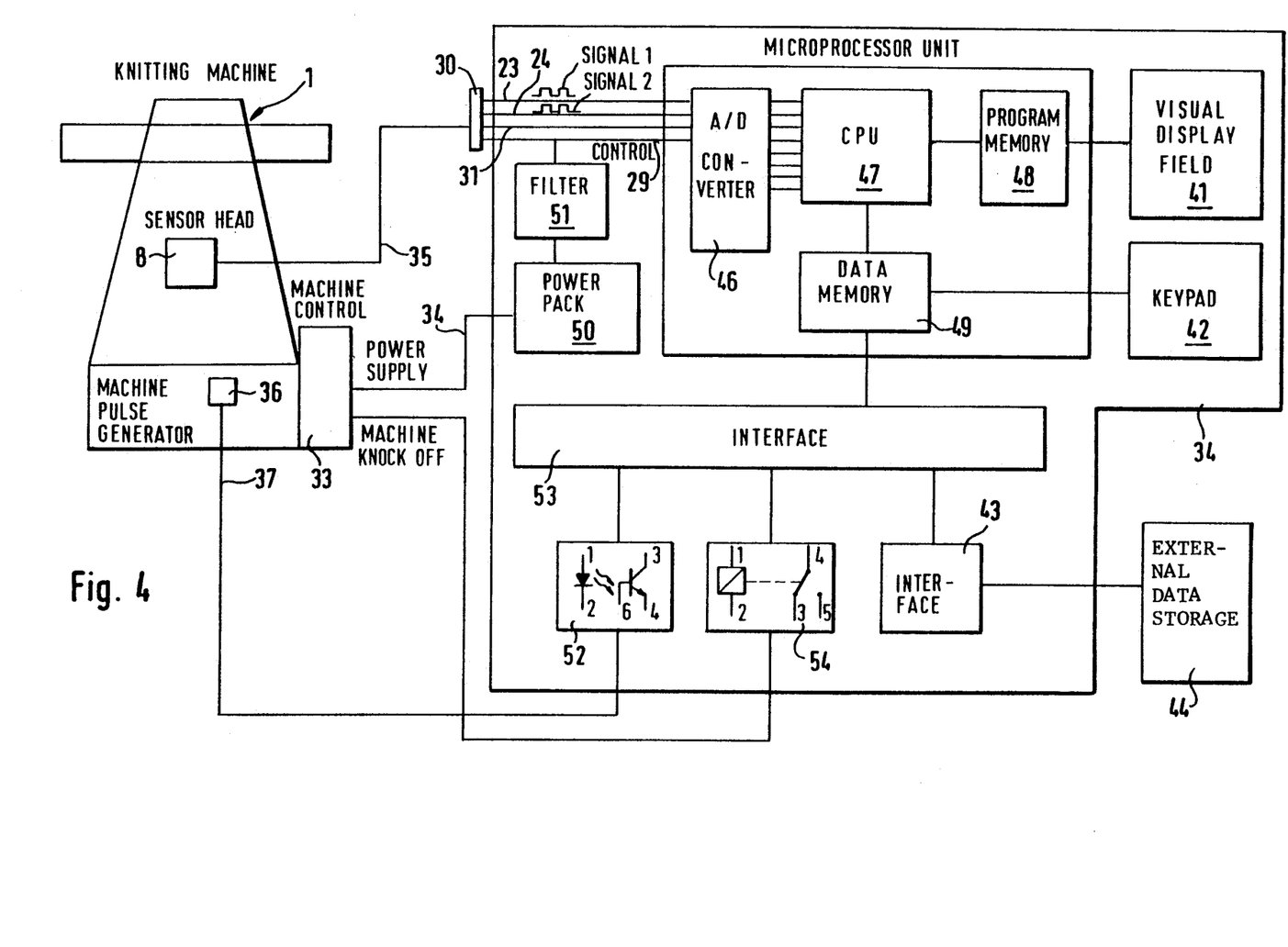

The fault signal analysis circuit of the control device 34 represented in FIG. 4 comprises the main groups analog/digital (A/D) convertor 46, microprocessor (CPU) 47, programme memory 48 and data memory 49. It also incorporates a power pack 50 connected to the mains supply line 34, which provides the power supply for the sensor head 8 and the various elements of the electronic fault signal analysis circuit via an appropriate powerline filter 51 and line 29.

The analog fault signals emanating from the sensor head 8 via the signal lines 23, 24 and the control line 31 or the analog control signal are passed to the four-channel analog/digital convertor 46 and here digitised appropriately for the processor. The subsequent microprocessor 47 analyses these digitised values received and files the data obtained from the analysis-classified according to type of fault-in the preferably non-transient data memory 49, through which data entry is also performed via the entry keypad 42. The visual display field 41 receives its data from the programme memory 48 correspondingly supplied by the microprocessor 47.

The synchronisation pulses necessary for synchronising the processing procedure of the fault signal analysis with the rotational movement of the tubular fabric 5 and produced by the machine pulse generator 36 in the form of an inductive proximity initiator, transmitted via the line 37 are passed via an electro-optical signal convertor circuit 52 to an interface 53 in the control device 34, by which a knock-off or stop-motion control circuit 54 used for stopping the circular knitting machine in the event of a fault and the V24 interface 43 are also connected to the microprocessor 47.

The analysis of the data transmitted from the A/D convertor 46 to the microprocessor 47 is performed using a software programme which will be described briefly in the following. This software programme performs a fault analysis by the following principle:

The fault signals passed via the signal lines 23, 24 indicate that in at least one of the light detectors 16 in group I or group II or in at least two light detectors 16 in the two groups I and II a change in the reflectance phenomena of the textile surface being scanned has occurred. These fault signals allocated to the separate groups (I, II) provide information not only on the occurrence of any fault, but also on the type of fault. For this purpose the following criteria are assessed:

a) The amplitude of the fault signal: It is established whether or not the amplitude lies above a prescribed threshold, with the possibility of different threshold values being prescribed for different types of faults, i.e. for spot faults or long faults. If the amplitude lies below the lowest threshold value then no fault is present and the fault signal remains ignored.

b) The term of the fault signal: It is established whether or not the signal length (term) exceeds a specific time threshold. Different thresholds can similarly be adopted for the different types of faults. If the signal term lies below the lowest threshold value then similarly no fault is present; the fault signal remains ignored because it is assumed that it is due merely to a short-term interference (e.g. electrical interference or thick place in the yarn etc.).

Based on the observation that the vast majority of long faults are narrower than spot faults, because for example runs are limited to the width of one wale of stitches whilst holes caused by a broken thread cover the width of several adjacent wales, the analysis of the signal term already provides an initial basis for distinguishing between the types of faults. If in fact the preset appropriately adopted threshold term is within a short period of time, then this suggests a long fault, whilst if a specific (possibly different) threshold term is exceeded by a longer period of time the presence of a long fault is probable.

c) Combined occurrence of fault signals (logic window): If the fault signals allocated to the groups (I, II) occur together, then this indicates that the zone of the textile fabric surface being scanned and in which a change in reflectance phenomena is established extends over a length affecting the two groups I, II of light detectors 16. If therefore the logic AND-condition of a repeating fault is satisfied for the two group-specific fault signals, then a long fault is probably present. If on the other hand the test shows that the OR-condition is satisfied then a spot fault is involved. If the rotating tubular fabric 5 scanned in the strip-form sensing zone 22 of the sensor head 8 contains a run, i.e. a long fault, then the affected light detectors 16 of the sensor head 8 in groups I, II only emit a fault signal simultaneously if the run is aligned exactly parallel to the axis of the strip-form scanning zone 22. In actual fact, however, due to the fabric take-up and the consequent deformation of the tubular fabric in being transformed from the cylindrical to the laid-flat form, certain distortions of the knitted fabric are in principle unavoidable. In other words, depending on the point of attachment of the sensor head 8 relative to the needle cylinder, the wales of stitches are laid somewhat obliquely or curvilinearly in relation to the axis of the scanning zone. When the simultaneous occurrence of fault signals in more than one group is analysed as an indication of the presence of a long fault, then a more positive fault identification would be ensured only under the provision that the longitudinal stitches (e.g. runs) occur in the scanning zone exactly parallel to the axis of the strip-form scanning zone, i.e. the row of light detectors 16. The occurrence of every oblique position results in the light detectors 16 in the separate groups responding at times staggered in relation to each other, with the consequence that without special precautions, the long fault would be erroneously interpreted as a succession of spot faults.

In order to prevent this and also to ensure unequivocal fault identification in the event of pulled stitches, e.g. in runs at an oblique angle, in the analysis of the logic window it is investigated whether consecutive fault signals of the two groups occur within a prescribed measuring period, which corresponds to the maximum time shift between the occurrence of the two fault signals to be expected for the respective type of fault. In practice this can happen in such a way that the two fault signals are held in store separately for a predetermined period and only then analysed for mutual occurrence.

If they occur together within this period of time, then a long fault is probably involved (AND-requirement satisfied). If only one of the two signals occurs, a spot fault is probably present (OR-requirement satisfied).

d) Periodically repeating fault: The periodic repeat of a fault is recorded for every revolution of the machine, with the option of taking measures to either stop the machine the first time the fault is repeated or only after a number of revolutions in which the fault is repeated.

If a fault repetition occurs in successive machine revolutions then a long fault is involved. If no such fault repetition is established then as a rule a spot fault is present.

The faults detected are recorded and stored separately according to types of faults and where required displayed on the visual display field 41. Counters are provided which record the total number of faults per fabric roll (classified by type of fault or in total), and the number of faults per unit time (similarly classified by type of fault or in total) etc. and their current counter status can be interrogated in the display field 41 by the operative via the entry keypad 42. The machine stop-motion knock-off 54 and where required also alarm devices are energized via the interface on the basis of the number and type of faults detected, with provision being possible for the needle cylinder coming to rest in a position in which for example a broken needle lies opposite a needle door when the machine stops.

In the microprocessor 47 the control signal received via the control line 31 is tested for whether or not the control current of the brightness regulator 25 (FIG. 3) lies within the prescribed tolerances. As soon as one of the threshold tolerances is exceeded and consequently the optical sensing conditions become intolerable, the machine knock-off 54 is actuated via the interface 43 or an alarm signal displayed in the visual display field 41.

The flow diagram for an appropriate programme for the microprocessor 47 is illustrated in FIGS. 6 to 9. Following switching on, the microprocessor first runs a non-recurring start-up routine. In an internal priming phase the programme or command sequence counters are set at the start value. The control or status indices are set in accordance with the data prescribed in the RAM or ROM memory of the microprocessor 47. Once this start-up routine is completed, the "TKS" fault signals emanating from the sensor head 8 via the A/D convertor 46 are read in at 60, which are identified by TKS-1 for group I and TKS-2 for group II.

Figure 6:
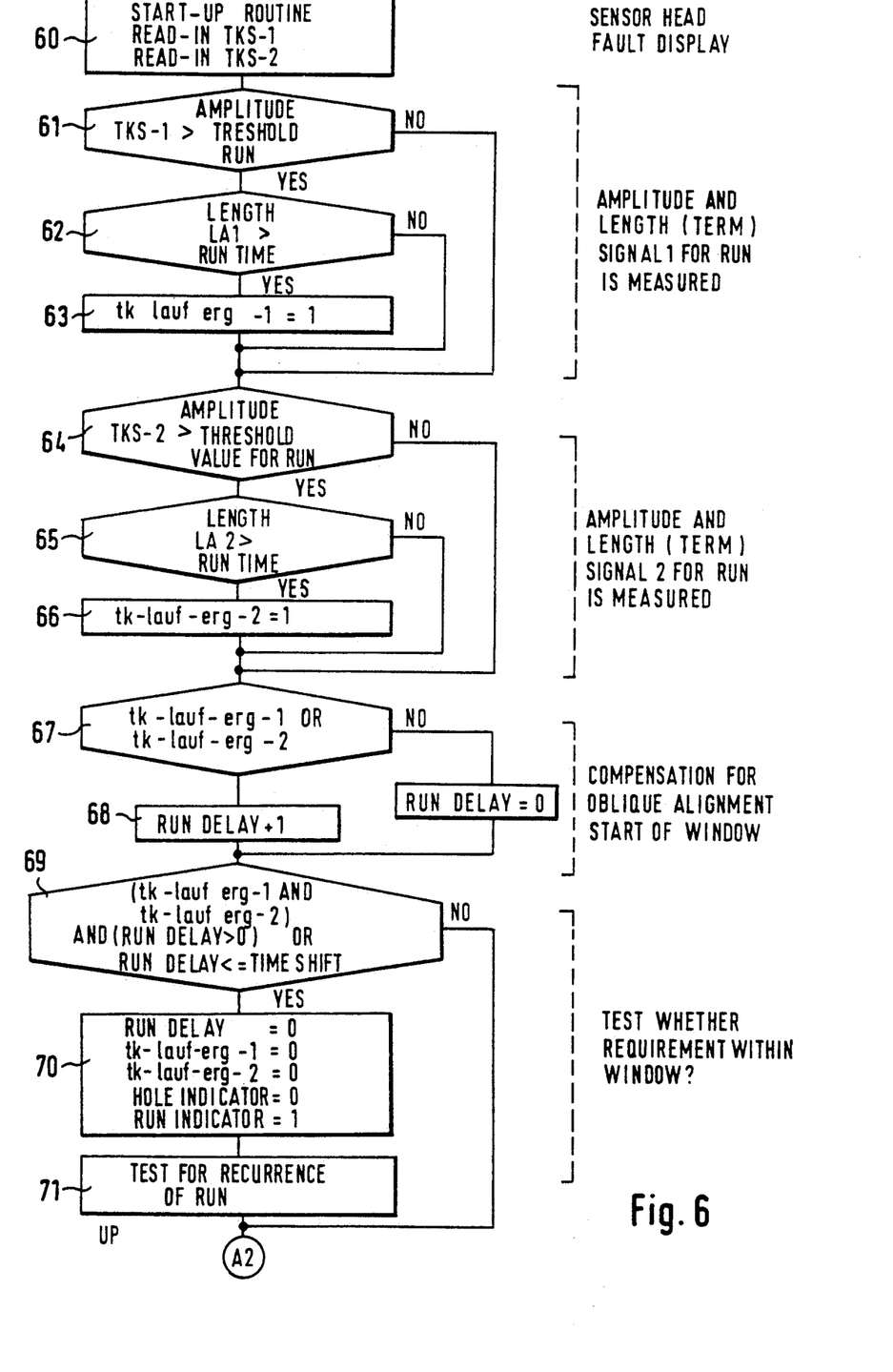

A test is then performed by 61 of whether or not the amplitude of the fault signal of group I exceeds the amplitude threshold for a run, i.e. for a long fault. If yes, it is established at 62 whether the signal term or length LA 1 of the signal TKS-1 (of group I) lies above the prescribed time threshold for runs. If the two tests give a positive result, then this is held in interim store at 63, i.e. "TK-Lauf(masche)-Erg(ebnis)-1" is set at 1.

Then the same test is performed at 64, 65 for the fault signal TKS-2 of group II, the positive result of which is similarly held in interim store at 66 where applicable.

The logic window provided for the analysis of the criteria for distinguishing the types of faults now begins at 67. For this purpose it is first established whether the preceding tests on the fault signals TKS-1 or TKS-2 have produced a positive result and accordingly whether or not TK-Lauf-Erg for group I or group II is verified or not. If yes, at 68 an index of 1 is applied for a delay count applicable to runs, if no the delay count is returned to zero.

This is therefore where the compensation takes place for any oblique positioning of a run in relation to the scanning field of the sensor head 8. The results of the previous test of the signals TKS-1 and TKS-2 are thus first held separately in interim store and only then analysed for their mutual occurrence.

For this purpose it is investigated at 69 whether the stored results TK-Lauf-Erg-1 and TK-Lauf-Erg-2 satisfy the AND-requirement and also whether as a further AND-requirement the delay applicable to runs is greater then 0 or < a prescribed time shift. This time shift is produced from the specific type of knitted fabric to be scanned. It corresponds for example to the time taken by three adjacent wales of stitches to pass through the strip-form scanning zone 22 of the sensor head 8.

If the test shows that the three above AND-requirements are satisfied, then a run is present. A "run" indicator is set at 1 whilst the remaining parameters are reset at 0, which takes place at 70. In the course of the programme a test is then performed at 71 with the aid of a sub-programme of whether the run fault detected is repeated at the next machine revolution. If yes, then for example the machine knock-off 54 can be actuated. Simultaneously a "run" display appears in the display field 41. Counters for the total number of faults, for the total number of run faults, for the total number of faults or run faults per unit time and so forth continue to operate. Part of this programme procedure is briefly described with the aid of the following identification of a spot fault ("hole").

If the AND-requirement is not satisfied at 69 then for the purpose of safety a test is again performed at 72 (FIG. 7) of whether the "run" delay is greater than the preset time shift. If yes, the requirements for the presence of a run are not definitively satisfied. All parameters are reset to 0 at 73.

Figure 7:
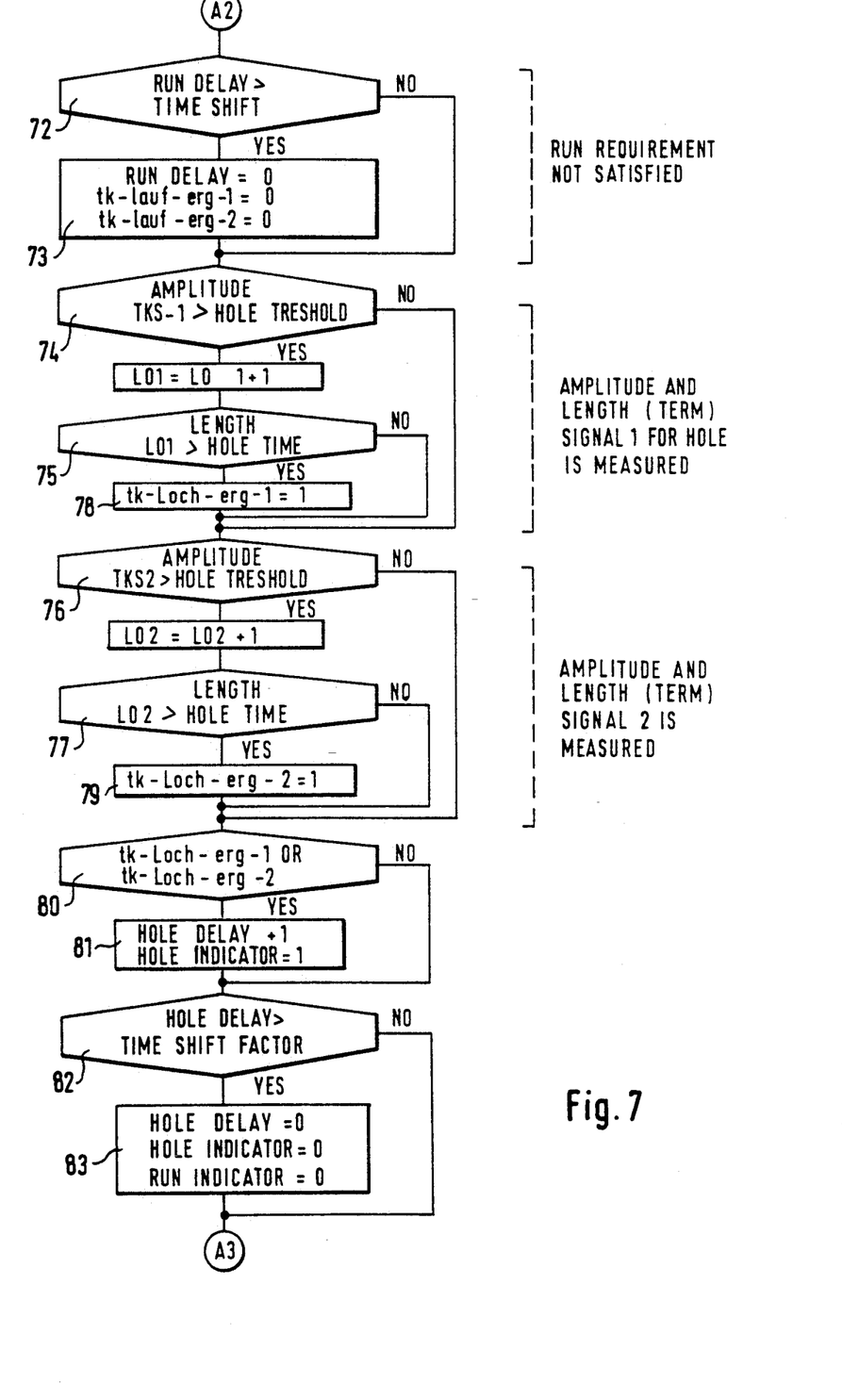

However, if it is established at 72 that the tested signals TKS-1 and TKS-2 have a greater time interval than the preset (maximum) time shift applicable to runs, then the test of the two signals immediately begins of whether they signify the presence of a spot fault, i.e. hole.

For this purpose at 74 and 76 a test is performed of whether or not the amplitude of the signal TKS-1 or TKS-2 exceeds an amplitude threshold prescribed for hole detection ("hole threshold"), whilst at 75, 77 a test of these two signals is performed for whether or not the signal term or length exceeds a prescribed time threshold applicable to hole detection.

The results of tk-Loch-Erg-1 and -2 are in turn held in interim store at 78, 79.

Finally at 80 it is established whether or not the results of the previous tests held in interim store satisfy the logic OR-requirement. If yes, an index for the delay applicable to hole detection is applied at 81, whereupon it is investigated at 82 whether the "hole" delay which is greater than the time shift prescribed for run detection, corresponding to three wales of stitches, multiplied by a factor is or is not exceeded.

This factor has the effect of expanding the time window, which prevents wide holes being counted more than once. If a "hole" delay is established which is greater than the time shift x the factor, then the measurement is discontinued. The parameters are set at zero at 83.

However, if the requirement is not satisfied at 82, i.e. if the signals still lie within the wider time window applicable to hole detection, then a test is again performed at 84 of whether the stored test results TK-Loch-Erg-1 and TK-Loch-Erg-2 satisfy the logic AND-requirement. If the answer is "yes" then a run is present, although its amplitude and term lie above the corresponding threshold values applicable to hole detection. Therefore at 85 the "run" indicator is set at 1, whilst the "hole" indicator is set at zero.

If the two results TK-Loch-Erg-1 and TK-Loch-Erg-2 do not satisfy the logic AND-requirement, then for the purpose of safety a test for the OR-requirement is performed again at 86, and with a positive result the "hole" indicator at 87 is set at 1.

At this point in the programme the analysis of the fault signals supplied by the sensor head 8 is completed. The data memory now contains separate information of whether a spot fault or a long fault, i.e. a hole or a run, is present.

Figure 8:
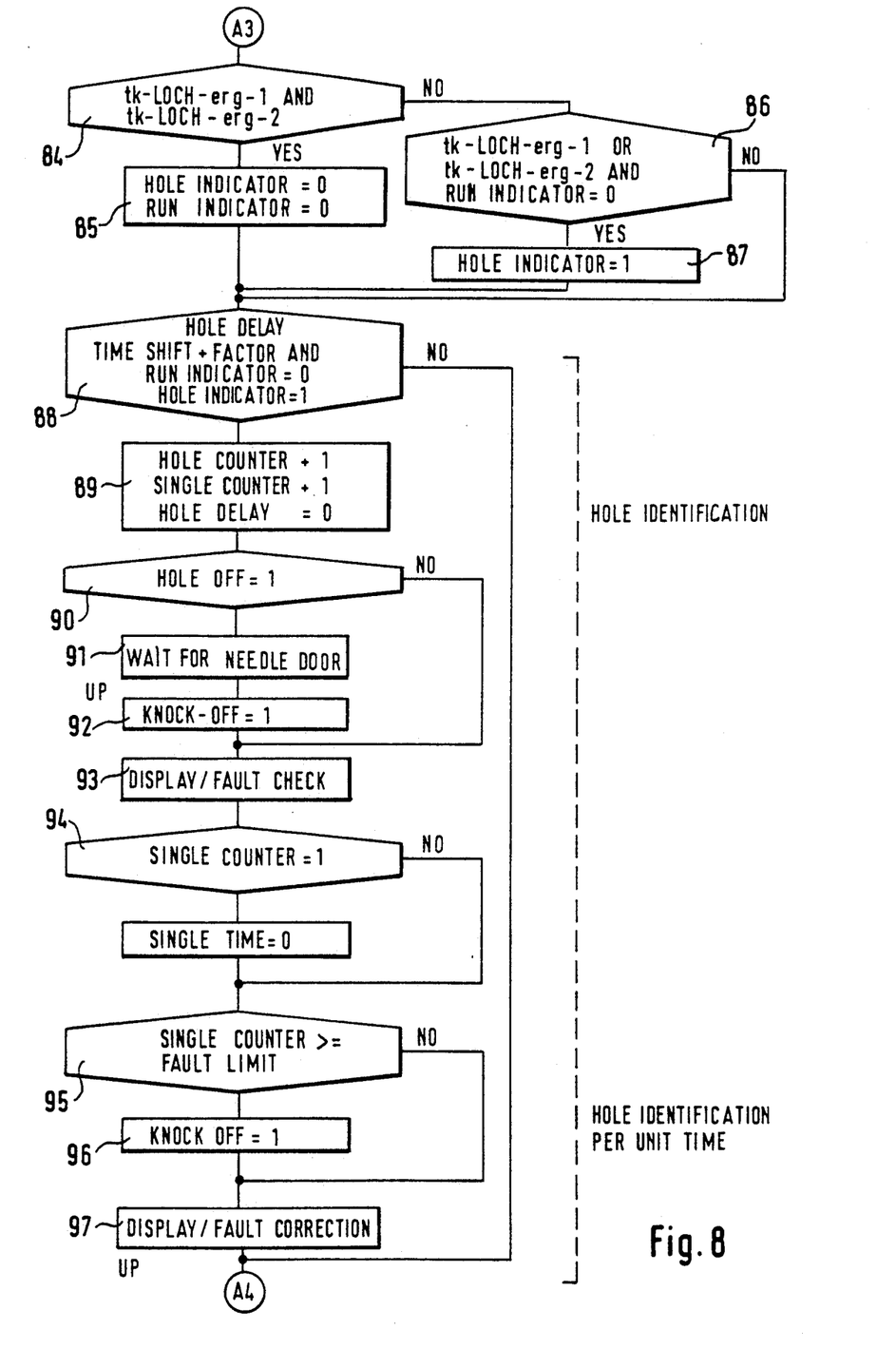

The further processing of the information thus obtained takes place for runs at 71 and for holes in the programme section briefly described in the following, which is provided in similar manner for run detection and is incorporated in 71. It is therefore sufficient to outline briefly solely this programme section for hole detection:

Following the programme stage previously described a test is again carried out at 88 of whether the "hole" delay is equal to the set time shift x the prescribed factor and whether the "run" indicator stands at zero or the "hole" indicator at "1". If this requirement is satisfied, then at 89 a counter giving the total number of holes—"hole counter"— and a single counter, together with a counter giving the total number of faults where required, each have an index of 1 applied. In the event of the machine knock-off 54 being having to be actuated following the occurrence of a hole, a corresponding command has been entered via the entry keypad 42. A test is therefore carried out at 90 of whether or not such a knock-off command "hole-off" is present. If yes, a knock-off routine is initiated at 91 which ensures that when the machine stops the needle cylinder comes to rest at a position predetermined in relation to the needle door, whereupon the knock-off is actuated at 92. Furthermore the display field 41 is energised by 93, giving a fault display and simultaneously requesting the operative to correct the fault.

It is frequently also desirable to be aware of, record and display on the display field 41 the faults detected per unit time-classified into spot faults or long faults.

This can take place in the further course of the programme at 94 (for holes), whilst at 95 a test is carried out of whether the number of faults detected exceeds a prescribed fault limit. If yes, the knock-off routine for the machine knock-off 54 is actuated at 96. In any case at 97 the display field 41 is energised for the corresponding fault display and request for fault correction.

The programme can additionally incorporate the facility for calling up a sub-programme for producing a display report, resetting the counters for the faults on arriving at the end of the fabric roll so that the number of faults per fabric roll can be given, and triggering an exit routine and a start-up routine for the restarting of the machine following a stoppage due to other causes etc. These programme stages are not further illustrated in detail.

Figure 9:
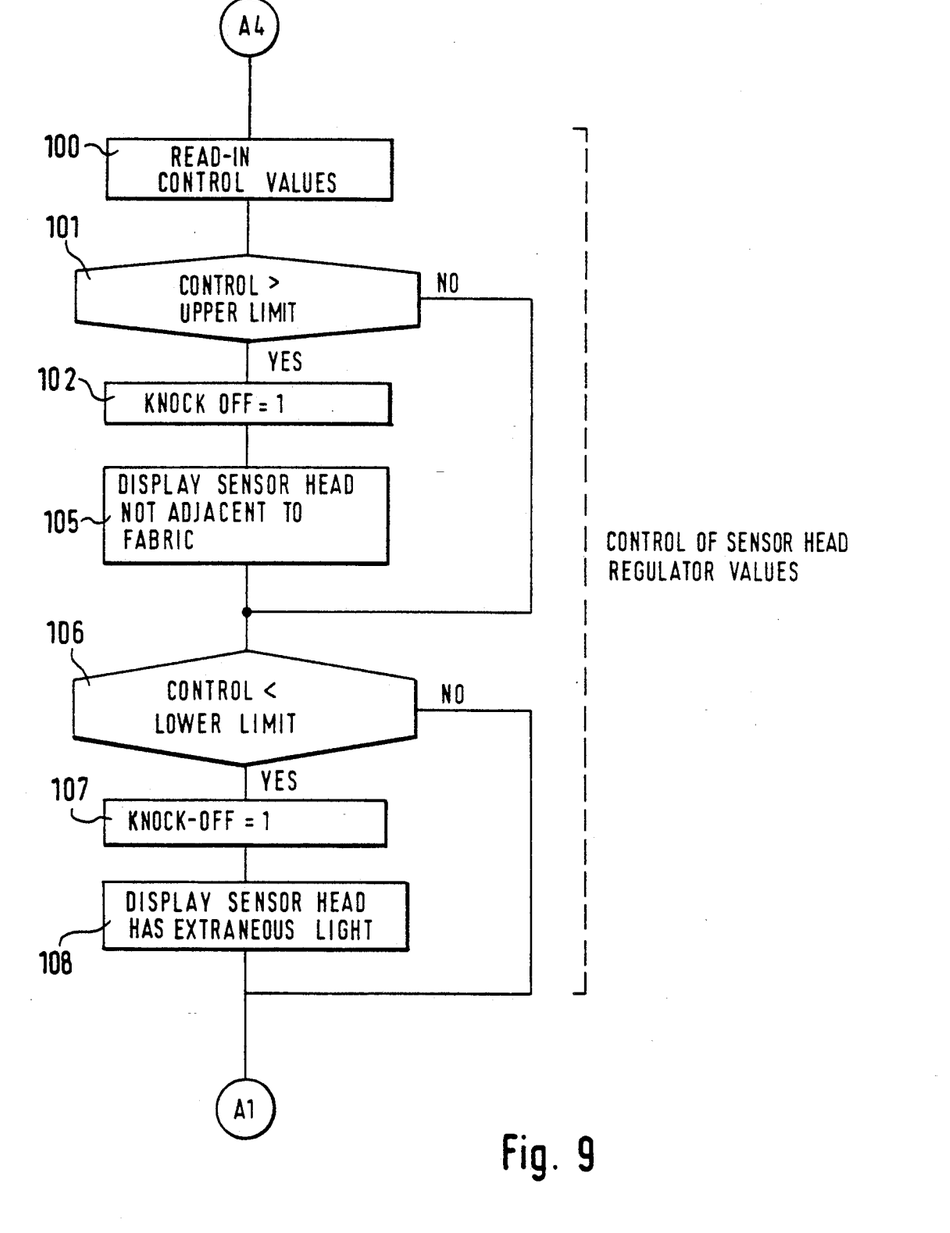

FIG. 9 simply explains briefly how the control signals for the brightness values of the illumination of the textile fabric being scanned and transmitted via the control line 29 from the sensor head 8 are processed. These control values are read in at 100. A test is carried out at 101 of whether they exceed a prescribed upper limit. If yes, the machine knock-off 54 is actuated at 102, whilst simultaneously the display field 41 is provided with corresponding information by 105 so that it displays the probable cause of fault, namely that the sensor head is not adjacent to the fabric.

At 106 the corresponding test relating to the lower limit takes place, which with a positive result similarly causes machine knock-off at 107, whilst at 108 the display field 41 is energised in such a way that it displays the probable cause of fault, namely that the sensor head has extraneous light.

The programme procedure is thus completed, the programme returns to the start following the start-up routine.

Finally further programme sections can be incorporated in the programme which ensure that an entry of commands, parameters and suchlike made via the entry keypad 42 can only take place whilst the machine is stationary, in order thus to avoid abortive stoppages of the machine in production occurring due to incorrect operation of the control device 34.

The new process has been outlined in the above with the example of a circular knitting machine with rotating needle cylinder. In principle it is naturally also suitable for circular knitting machines and circular warp knitting machines with stationary needle cylinder (then with circulating sensor head 8) and for weaving machines. It is only necessary to ensure that there is relative movement between the scanning zone 22 of the sensor head and the surface of the textile fabric being scanned and that this scanning movement occurs at a prescribed preferably constant speed.

A suitable CPU 47 is: INTEL 8051

Suitable interfaces 43, 53 are: Communication interface Maxim Type Max 232 and Relais driver ULN 2000

We claim:

1. A method for the detection of faults in a length of textile fabric, especially in a tubular knitted fabric produced on a circular knitting machine or circular warp knitting machine, comprising electro-optically scanning, in strip form, a length of fabric in at least one zone, said zone being in strip form, by a sensing means;

deriving electrical sensing signals characterizing the condition of the length of fabric at a number of sensing points lying within said strip form zone;

maintaining a predetermined speed between the length of fabric and the sensing means in the direction transverse to the strip form zone during sensing, whereby the zones being scanned in the length of fabric are scanned a number of times;

said method comprising further, in accordance with the invention, analyzing the signals in such a way that a distinction is made between different forms or different sizes of types of faults, and providing separate output signals in which the type of fault is separately identified, said analyzing step including collecting the sensing signals characterizing the individual sensing points into at least two group-specific fault signals;

processing and analyzing the fault signals separately by amplitude, term or duration of signals, and determining non-repeating or repeating occurrence of fault signals of the separate groups;

measuring and establishing by this analysis and by the fault analysis an identification of the type of signal wherein a) a spot type fault is identified if
   (i) in the case of at least one fault signal varying in amplitude from a prescribed first amplitude threshold value,
   (ii) the signal term exceeds a predetermined first time threshold value by at least a prescribed first period of time, and
   (iii) without a number of fault signals occurring together within a measuring period;

b) a long type fault if
   (i) in at least two fault signals varying in amplitude from a prescribed second amplitude threshold value,
   (ii) the signal term exceeds a predetermined second time threshold value by at least a period of time which is shorter than said first time period, and
   (iii) at least two fault signals occur together within a measuring period; and c) unless the signals had all the characteristics of (a) above or all of the characteristics of (b) above are sensed, identifying the signals as not representing a fault; and providing separate output signals controlling an output means in which the types of faults are separately identified with respect to (a) or (b).

2. Method in accordance with claim 1, further including the steps of additionally analyzing the signals with respect to whether a periodically occurring repeating signal is present in at least one operating cycle, optionally a revolution of the circular knitting machine; and utilizing occurrence of an established periodically occurring signal as an additional criterion for the identification of a fault as a long type fault.

3. Method in accordance with claim 1, characterized by the fault signals each being held separately in the interim store at least for a predetermined period and only then investigated for their recurrence.

4. Method in accordance with claim 1, characterized by the first and the second amplitude threshold values being equal.

5. Method in accordance with claim 1, characterized by the first and the second amplitude threshold values differing the one from the other.

6. Method in accordance with claim 1, characterized by the first and the second time threshold values being equal.

7. Method in accordance with claim 1, characterized by the first and the second time threshold values differing the one from the other.

8. Method in accordance with claim 1, characterized in that the measuring time periods for the identification of spot and long faults are of different lengths.

9. Method in accordance with claim 1, used in a knitting machine producing knit fabric, characterized in that the measuring period for long faults when scanning knitted fabric corresponds approximately to the time required for three wales of stitches to pass through the strip-form scanning zone.

10. Method in accordance with claim 1, characterized by forming a weighted cumulative signal from the sensing signals and adjusting the electro-optical sensing means to constant prescribed optical sensing conditions as a function of this cumulative signal.

11. Method in accordance with claim 10, characterized by monitoring the weighted cumulative signal by it lying within prescribed tolerance limits and emitting a control signal when the cumulative signal falls above or below one of these tolerance limits.

12. Method in accordance with claim 1, characterized by the sensing points being geometrically arranged in a row.

13. Method in accordance with claim 1, characterized by information on the faults identified, obtained from the analysis of the fault signals and classified according to type of fault, being held in store in separate data memories and being recalled from these memories for display or further processing.

14. Method in accordance with claim 1, characterized by information on the faults identified, classified by types of faults, being passed to external data recording devices via a series data interface.

15. Method in accordance with claim 14, characterized by fault parameters being programmed via the series data interface.

16. Method in accordance with claim 1, for use in a textile manufacturing machine, further including the step of sensing the operating speed of said machine, and providing a pulse train representative of the operating speed or passage through operating cycles of said machine; and controlling said first and second periods of time as a function of the operating speed or passage through operating cycles of the machine, as determined by the pulse repetition rate of the pulses.

17. A system for the detection of faults in a length of textile fabric, especially in a tubular knitted fabric produced on a circular or circular warp knitting machine, and for distinguishing between spot type faults or holes and long type faults or runs, said system comprising electro-optical scanning means arranged in strip form to scan a length of fabric in at least one zone, wherein said zone is in strip form, and deriving electrical sensing signals characterizing the condition of the length of fabric from a number of sensing points within said strip form zones as scanned by said electro-optical scanning means;

said fabric and said scanning means being relatively movable with respect to each other at an essentially uniform, predetermined rate, between the length of fabric and the sensing means in a direction transverse to the strip form zone during sensing, whereby the zones being scanned in the length of fabric are scanned a plurality of times; and a control, evaluation and analyzing unit analyzing the signals from said scanning means, and separating said signals into two group-specific fault signals, in which the individual signals are analyzed separately by amplitude, duration of signals, and repeating or non-repeating occurrence of fault signals of the separate groups, said control, evaluation and analyzing unit providing separate output signals controlling output means in which the faults are separately identified as
a) a spot type fault is identified if
  (i) in the case of at least one fault signal varying in amplitude from a prescribed first amplitude threshold value,
  (ii) the signal term exceeds a predetermined first time threshold value by at least a prescribed first period of time, and
  (iii) without a number of fault signals occurring together within a measuring period;
b) a long type fault if
  (i) in at least two fault signals varying in amplitude from a prescribed second amplitude threshold value,
  (ii) the signal term exceeds a predetermined second time threshold value by at least a period of time which is shorter than said first time period, and
  (iii) at least two fault signals occur together within a measuring period; and
c) unless the signals had all the characteristics of (a) above or all of the characteristics of (b) above are sensed, identifying the signals as not representing a fault; and providing separate output signals controlling an output means in which the types of faults are separately identified with respect to (a) or (b).

18. The system of claim 17, in combination with a fabric producing machine,
wherein said fabric producing machine comprises a pulse source (36) coupled to said control, evaluation and analyzing unit (34) and providing data regarding the operating speed of said machine, said control evaluation and analyzing unit calculating the length of fabric passing beneath the sensing head during said respective first and second periods of time.

19. The system of claim 18, wherein said control, evaluation and analyzing unit (34) comprises a short-term or interim memory or data store (49) storing fault signals occuring during one operating cycle of the machine, as determined by pulses from said pulse source (36) for comparison with subsequent signals of a similar type during subsequent operating cycles of the machine.

20. The system of claim 17, further including display means (41) displaying the types of faults or absence of faults detected by said sensing means, as analyzed by said control evaluation and analyzing unit, said display means displaying the presence of short faults or holes and long faults or runs, indicative of a needle malfunction in a knitting machine, separately.

* * * * *